United States Patent
Lee et al.

(10) Patent No.: US 11,519,037 B2
(45) Date of Patent: Dec. 6, 2022

(54) NON-INVASIVE TEST TO PREDICT RESPONSE TO THERAPY IN COLORECTAL CANCER PATIENTS

(71) Applicant: Roche Sequencing Solutions, Inc., Pleasanton, CA (US)

(72) Inventors: John Lee, Walnut Creek, CA (US); Alexander Lovejoy, Newark, CA (US); John Palma, Alamo, CA (US); Ulrich-Peter Rohr, Loerrach (DE); Lijing Yao, Foster City, CA (US); Stephanie Yaung, San Jose, CA (US)

(73) Assignee: ROCHE SEQUENCING SOLUTIONS, INC., Pleasanton, CA (US)

( * ) Notice: Subject to any disclaimer, the term of this patent is extended or adjusted under 35 U.S.C. 154(b) by 501 days.

(21) Appl. No.: 16/534,272

(22) Filed: Aug. 7, 2019

(65) Prior Publication Data
US 2019/0360060 A1  Nov. 28, 2019

Related U.S. Application Data

(63) Continuation of application No. PCT/EP2018/052751, filed on Feb. 5, 2018.

(60) Provisional application No. 62/455,994, filed on Feb. 7, 2017.

(51) Int. Cl.
*C12Q 1/6886* (2018.01)
*G16B 20/20* (2019.01)

(52) U.S. Cl.
CPC ........... *C12Q 1/6886* (2013.01); *G16B 20/20* (2019.02); *C12Q 2600/106* (2013.01); *C12Q 2600/156* (2013.01)

(58) Field of Classification Search
CPC .................................................. C12Q 1/6886
USPC ...................................................... 424/133.1
See application file for complete search history.

(56) References Cited

U.S. PATENT DOCUMENTS

2016/0032396 A1    2/2016  Diehn et al.

OTHER PUBLICATIONS

Tockman et al (Cancer Res., 1992, 52:2711s-2718s).*
Bratman, S. V. et al, Potential clinical utility of ultrasensitive circulating tumor DNA detection with CAPP-Seq, Expert Rev Mol Diagn, (2015), pp. 715-719, vol. 15 No. 6.
Cremolini, C. et al., FOLFOXIRI plus bevacizumab versus FOLFIRI plus bevacizumab as first-line treatment of patients with metastatic colorectal cancer: updated overall survival and molecular subgroup analyses of the open-label, phase 3 TRIBE study, Lancet Oncol, (2015), pp. 1306-1315, vol. 16.
Hurwitz, H. et al., Updated efficacy, safety, and biomarker analyses of STEAM, a randomized, open-label, phase II trial of . . . , Journal of Clinical Oncology, (2017), Suppl. 1, vol. 35 No.
International Search Report and Written Opinion, dated Apr. 20, 2018, in corresponding PCT/EP2018052751, filed Feb. 5, 2018, pp. 1-19.
Kidess-Sigal, E. et al, Enumeration and targeted analysis of KRAS, BRAF and PIK3CA mutations in CTCs captured by a label-free platform: Comparison to ctDNA and tissue in metastatic colorectal cancer, Oncotarget, (2016), pp. 85349-85364, vol. 7, No. 51.
Roche, Avenio ctDNA Surveillance Kit coverage for lung and CRC serial tumor burden monitoring, Tumor Burden Monitoring, Jul. 31, 2017, retrieved from the Internet, -.
Tan, C. R. C. et al., Circulating Tumor Cells Versus Circulating Tumor DNA in Colorectal Cancer: Pros and Cons, Current Colorectal Cancer Reports, (2016), pp. 151-161, vol. 12.
Tie J. et al, Circulating tumor DNA analysis detects minimal residual disease and predicts recurrence in patients with stage II colon cancer, Science Translational Medicine, (2016), pp. 346ra92-346ra92, vol. 8, No. 346.
Vogel, M., Somatic Mutation Detection in Cancer, Biosb. (NL), Dec. 31, 2016, retrieved from the Internet, -.

* cited by examiner

*Primary Examiner* — Sean E Aeder
(74) *Attorney, Agent, or Firm* — Eric Grant Lee; Olga Kay

(57) ABSTRACT

The invention is a method of predicting response to therapy in a colorectal cancer patient, the method comprising analysis of circulating tumor DNA from a patient's sample.

4 Claims, 4 Drawing Sheets

RAS WT

Tissue samples (n=55)

Pretreatment plasma samples (n=65)

TP53 Mutant

Tissue samples (n=75)

Pretreatment plasma samples (n=71)

Grouped by pretreatment allele frequencies (AF) (n=118)

Grouped by treatment, all less than median AF (n=59)

US 11,519,037 B2

NON-INVASIVE TEST TO PREDICT RESPONSE TO THERAPY IN COLORECTAL CANCER PATIENTS

CROSS-REFERENCE TO RELATED APPLICATIONS

This patent application is a continuation of International Patent Application No. PCT/EP2018/052751 filed Feb. 5, 2018, which claims priority to and the benefit of U.S. Provisional Application No. 62/455,994, filed Feb. 7, 2017. Each of the above patent applications is incorporated herein by reference as if set forth in its entirety.

FIELD OF THE INVENTION

The invention relates to the field of oncology. More specifically, the invention relates to the field of nucleic acid-based testing of cancer patients.

BACKGROUND OF THE INVENTION

It is important to provide effective therapy to metastatic colorectal cancer (mCRC) patients as they have poor 5-year survival. Currently, mCRC patients receive either targeted anti-EGFR therapy plus chemotherapy based on RAS wild-type status or all comers are eligible for anti-angiogenesis plus chemotherapy. Many of the CRC patients are diagnosed with metastatic disease after progression from earlier stage disease. For some patients, a tissue sample from the earlier stage is not available or does not represent the patient's current disease state. Many patients newly diagnosed with mCRC are considered inoperable. There is a need for a reliable way to access the tumor content of the patients for whom a tumor sample is not available in order to design proper therapy.

SUMMARY OF THE INVENTION

In some embodiments, the invention is a method for identifying a colorectal cancer patient in stage II, III or IV as likely to positively respond to a therapy regimen with increased progression-free survival (PFS), the method comprising the steps of: providing a cell-free blood sample obtained from the patient; determining the sequence of at least a portion of each of the biomarkers listed in Table 1; measuring the frequency of mutant alleles; identifying the patient as likely to positively respond to a therapy regimen if the frequency of mutant alleles is below a median documented for colorectal cancer patients at the same stage; or identifying the patient as not likely to positively respond to a therapy regimen if the frequency of mutant alleles is above a median documented for colorectal cancer patients at the same stage. The patient can be a stage II, III or IV colorectal cancer patient. In some embodiments, the method further comprises a step of administering therapy if the patient is identified as likely to positively respond to a therapy regimen. The therapy regimen may be treatment with FOLFOXIRI-bevacizumab or treatment FOLFOX-bevacizumab. The treatment with FOLFOXIRI-bevacizumab may be concurrent or sequential.

In some embodiments, the invention is a method for identifying a colorectal cancer patient in stage II, III or IV as likely to positively respond to a therapy regimen with increased progression-free survival (PFS), the method comprising the steps of: providing a cell-free blood sample obtained from the patient; determining the mutation status of one or more genes selected from KRAS, BRAF, TP53 and PIK3CA; identifying the patient as likely to positively respond to a therapy regimen if the genes KRAS, BRAF and PIK3CA are wild-type and gene TP53 is mutant; or identifying the patient as not likely to positively respond to a therapy regimen if the genes KRAS, BRAF and PIK3CA are mutant and gene TP53 is wild-type. The therapy regimen is selected from concurrent and sequential FOLFOXIRI-bevacizumab.

In some embodiments, the invention is a method of treatment of a colorectal cancer patient in stage II, III or IV comprising the steps of: providing a cell-free blood sample obtained from the patient; determining the sequence of at least a portion of each of the biomarkers listed in Table 1; measuring the frequency of mutant alleles; identifying the patient as likely to positively respond to a therapy regimen if the frequency of mutant alleles is below a median documented for colorectal cancer patients at the same stage; or identifying the patient as not likely to positively respond to a therapy regimen if the frequency of mutant alleles is above a median documented for colorectal cancer patients at the same stage; administering the therapy regimen to the patient identified as likely to positively respond to the therapy. The patient may be a stage II, III or IV colorectal cancer patient. In some embodiments, the therapy regimen is selected from concurrent and sequential FOLFOXIRI-bevacizumab.

In some embodiments, the invention is a computer system designed to implement an algorithm for detecting mutations in a sample from colorectal cancer patient, wherein the algorithm analyses sequencing data on biomarkers from Table 1 and contains one or more steps selected from mutation detection, mutation frequency scoring, controlling for germ-line variation, error correction and final determination whether the sample is mutation-positive.

DETAILED DESCRIPTION OF THE INVENTION

Definitions

Figure 1:
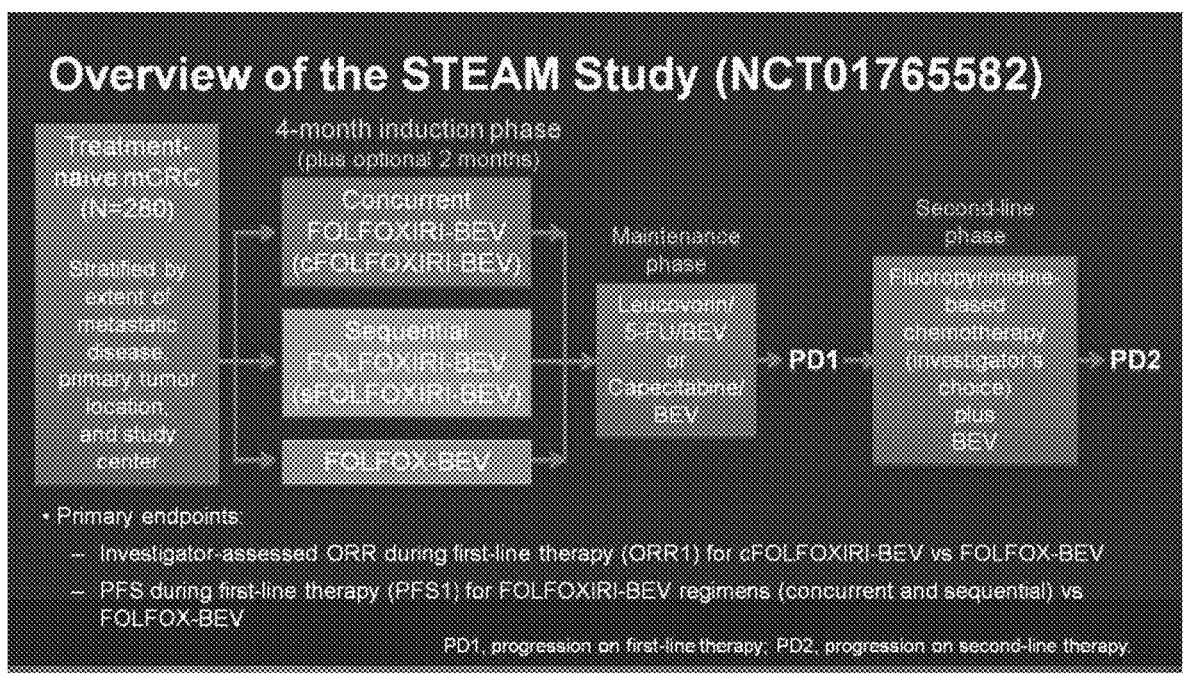
FIG. 1 illustrates the design of the therapy response prediction study.

The following definitions are not limiting but merely aid in understanding this disclosure.

The term "RFS" is used herein to describe the time of Recurrence Free Survival for a patient.

The term "TTR" is used herein to describe the Total Time to Recurrence for a patient.

The term "OS" is used herein to describe the time of Overall Survival for a patient.

The term "CAPP-Seq" is used herein to describe a method of analyzing cell-free tumor DNA in a patient disclosed in U.S. patent applications Ser. Nos. 14/209,807, 14/774,518 and International Application Ser. No. PCT/US2015/049838 titled "Identification and Use of Circulating Tumor Markers."

The term "R0 patient" is used herein to describe a patient having clear histological margins from resected tissue.

The term "R1 patient" is used herein to describe a patient having microscopic residual disease in surgically resected tissue.

The term "circulating tumor DNA (ctDNA)" is used herein to describe a portion of cell-free DNA found in human blood plasma or serum that originates from the tumor. Circulating tumor DNA is distinguished from non-tumor DNA by the mutations characteristic of the tumor. In the context of the present invention, detecting ctDNA means detecting mutated cell-free DNA.

The term "biomarker" is used herein to describe a nucleotide sequence that contains information relevant to the biological or clinical phenomenon. For example, the information may be a mutation status of the sequence. The biomarker can be a gene (including coding sequence, regulatory sequence, intron or a splice site) or an intergenic region. The clinical phenomenon can be the presence of malignant cells, e.g., tumor cells in a patient's sample.

The invention describes methods of selecting a treatment regimen for a colorectal cancer (CRC) patient including a metastatic colorectal cancer (mCRC) patient.

In some embodiments, the invention uses a biomarker panel to identify somatic mutations and mutation burden in cancer-related genes by next-generation sequencing (NGS). In some embodiments, the invention utilized a blood sample from a patient. The sample can include any fraction of blood, e.g., serum or plasma, which contains cell-free DNA including circulating tumor DNA (cfDNA or ctDNA). In some embodiments, the sample is taken serially at various times during treatment, e.g., before and after surgery or before, after and during a chemotherapy regimen. In some embodiments, tissue sample is available for comparison with the blood sample. The tissue or blood sample can be collected by a suitable means that preserves the DNA therein, including formalin-fix paraffin-embedding (FFPE), fresh frozen tissue or blood tissue collected in a preservative medium.

In some embodiments, the invention utilizes a biomarker panel, including a gene panel or a mutation panel or a somatic variant panel. The mutations may include single-nucleotide variations (SNVs), deletions and insertions (indels) that correspond to on-sense missense and frame-shift mutations if they occur in the coding regions of genes. Other types of mutations include gene fusions and translocations. The selection, size and content of such panels has been described e.g., in U.S. patent applications Ser. Nos. 14/209,807, 14/774,518 and International app. No. PCT/US2015/049838 titled "Identification and Use of Circulating Tumor Markers." In some embodiments, the invention includes determining the sequence of the biomarkers in the panel, e.g., the genes listed in Table 1. In some embodiments, the entire sequence of a gene is determined. In other embodiments, the entire coding sequence of a gene is determined. In other embodiments, only the sequence of a portion of the gene known to undergo mutagenesis in cancer is determined. In yet other embodiments, the biomarker is not associated with a coding sequence but is associated with a regulatory sequence or a sequence of unknown function known to be mutated in human tumors.

In the context of the present invention, the sequence of a biomarker can be determined via any suitable method known in the art. The suitable method would have sufficient accuracy, e.g., sensitivity and specificity to detect rare sequences with a low rate of errors. In some embodiments, the sequencing method includes an error correction step, such as use of molecular barcodes, error stereotyping and other chemical or computation methods of error suppression as described e.g., in see the patent applications "Identification and Use of Circulating Tumor Markers", supra. The sequencing method may include a massively parallel sequencing method, including an array based sequencing (Illumina, San Diego, Calif.), an emulsion-based sequencing (ThermoFisher, Waltham, Mass.) an optical measurement based sequencing (Pacific BioSciences, Menlo Park, Calif.) or a nanopore-based sequencing (Roche Sequencing Solutions, Santa Clara, Calif.).

In some embodiments, the invention utilizes a biomarker panel, such as AVENIO® ctDNA Analysis Kit (Roche Sequencing Solutions, Inc., Pleasanton, Calif.) that is capable of analyzing the blood of patients after surgery to identify whether patients have circulating tumor DNA (ctDNA). The composition of the biomarker panel in AVENIO® ctDNA Analysis Kit (expanded panel) is shown in Table 1.

TABLE 1

Composition of the biomarker panel

| APC | KRAS | ABL1 | FGFR3 | JAK3 | RAF1 |
|---|---|---|---|---|---|
| BRCA1 | MET | AKT1 | FLT1 | KDR | RNF43 |
| BRCA2 | TP53 | AKT2 | FLT3 | MAP2K1 | TERT promoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | |

In some embodiments, a panel of 77 genes listed in Table 1 is used. In some embodiments, the mutation status is determined in both pre- and post-chemotherapy plasma samples. In some embodiments, the treatment is selected from a two-agent combination of FOLFOXIRI or FOLFOX and bevacizumab (BEV). In some embodiments, the treatment with the two agents is concurrent. In some embodiments, the treatment with the two agents is consecutive. In some embodiments, the treatment is first-line treatment of mCRC.

In some embodiments, the method involves a step of comparing the mutation status of genes from Table 1 in matched tissue sample and plasma sample collected prior to the commencement of therapy (baseline samples). The comparison revealed a concordance rate of 83% across all genes and 91.5%-100% for known mCRC related biomarkers.

In some embodiments, the invention comprises the use of individual biomarkers to predict a patient's response to chemotherapy. Until the present disclosure, there have been no known somatic mutation predictors of mCRC patient response to cytotoxic chemotherapies in the first line setting. The inventors have evaluated a series of somatic mutations for predictive value as shown in Table 2. In the table, treatment A is concurrent treatment with FOLFOXIRI-bevacizumab (cFOLFOXIRI-BEV), treatment B is sequential treatment with FOLFOXIRI-bevacizumab (sFOLFOXIRI-BEV) and treatment C is treatment with FOLFOX-bevacizumab (FOLFOXI-BEV).

TABLE 2

| | Effect of specific mutations on treatment efficacy | | | | | | | | |
|---|---|---|---|---|---|---|---|---|---|
| | | Tissue (N = 118) | | | | Pre-Tx Plasma (N = 118) | | | |
| Gene | Comparison | N | Med PFS (mo) | PFS HR | p-val | N | Med PFS (mo) | PFS HR | p-val |
| KRAS | WT v MT | 60/58 | 12.8/9.5 | 0.801 | 0.3174 | 70/48 | 11.5/9.5 | 0.839 | 0.4280 |
| | A v C in MT | 15/16 | 16.9/8.1 | 0.446 | 0.1021 | 14/14 | 16.9/8.1 | 0.400 | 0.0929 |
| | B v C in MT | 27/16 | 8.3/8.1 | 0.950 | 0.8855 | 20/14 | 7.6/8.1 | 1.045 | 0.9164 |
| | A v C in WT | 21/21 | 13.4/8.1 | 0.450 | 0.0594 | 22/23 | 13.4/8.1 | 0.472 | 0.0548 |
| | B v C in WT | 18/21 | 16.1/8.1 | 0.363 | 0.0238 | 25/23 | 13.6/8.1 | 0.431 | 0.0248 |
| RAS* | WT v MT | 55/63 | 13.4/9.5 | 0.786 | 0.2827 | 65/53 | 12.2/9.5 | 0.784 | 0.2668 |
| | A v C in MT | 17/19 | 15.3/8.1 | 0.471 | 0.1052 | 16/17 | 15.3/8.1 | 0.502 | 0.1547 |
| | B v C in MT | 27/19 | 8.3/8.1 | 1.008 | 0.9803 | 20/17 | 7.6/8.1 | 1.108 | 0.7931 |
| | A v C in WT | 19/18 | 13.4/8.5 | 0.387 | 0.0382 | 20/20 | 18.4/8.5 | 0.380 | 0.0233 |
| | B v C in WT | 18/18 | 16.1/8.5 | 0.323 | 0.0152 | 25/20 | 13.6/8.5 | 0.386 | 0.0142 |
| BRAF | WT v MT | 113/5 | 10.9/6.2 | 0.492 | 0.1692 | 113/5 | 10.9/6.2 | 0.492 | 0.1692 |
| | A v C in MT | 3/1 | 8.0/NA | NA | NA | 3/1 | 8.0/NA | NA | NA |
| | B v C in MT | 1/1 | 3.3/NA | NA | NA | 1/1 | 3.3/NA | NA | NA |
| | A v C in WT | 33/36 | 16.9/8.1 | 0.444 | 0.0101 | 33/36 | 16.9/8.1 | 0.444 | 0.0101 |
| | B v C in WT | 44/36 | 11.5/8.1 | 0.667 | 0.1244 | 44/36 | 11.5/8.1 | 0.667 | 0.1244 |
| PIK3CA | WT v MT | 100/18 | 11.2/8.1 | 0.650 | 0.1602 | 101/17 | 10.9/9.1 | 0.679 | 0.2208 |
| | A v C in MT | 6/5 | 15.3/8.1 | 0.299 | 0.2282 | 5/4 | 15.3/8.1 | 0.611 | 0.6473 |
| | B v C in MT | 7/5 | 7.4/8.1 | 1.280 | 0.7828 | 8/4 | 7.4/8.1 | 1.943 | 0.4950 |
| | A v C in WT | 30/32 | 13.4/8.8 | 0.480 | 0.0243 | 31/33 | 16.9/8.1 | 0.458 | 0.0160 |
| | B v C in WT | 38/32 | 12.8/8.8 | 0.590 | 0.0656 | 37/33 | 12.2/8.1 | 0.590 | 0.0641 |
| TP53 | WT v MT | 43/75 | 10.4/10.9 | 0.867 | 0.5407 | 47/71 | 10.4/11.2 | 0.919 | 0.7117 |
| | A v C in MT | 26/23 | 16.9/8.1 | 0.402 | 0.0161 | 25/19 | 16.9/7.7 | 0.356 | 0.0098 |
| | B v C in MT | 26/23 | 11.5/8.1 | 0.559 | 0.0892 | 27/19 | 12.2/7.7 | 0.514 | 0.0627 |
| | A v C in WT | 10/14 | 15.3/8.8 | 0.444 | 0.1682 | 11/18 | 15.3/9.5 | 0.478 | 0.1655 |
| | B v C in WT | 19/14 | 10.7/8.8 | 1.002 | 0.9965 | 18/18 | 10.7/9.5 | 0.965 | 0.9326 |

*RAS is a combination of NRAS and KRAS

Figure 2:
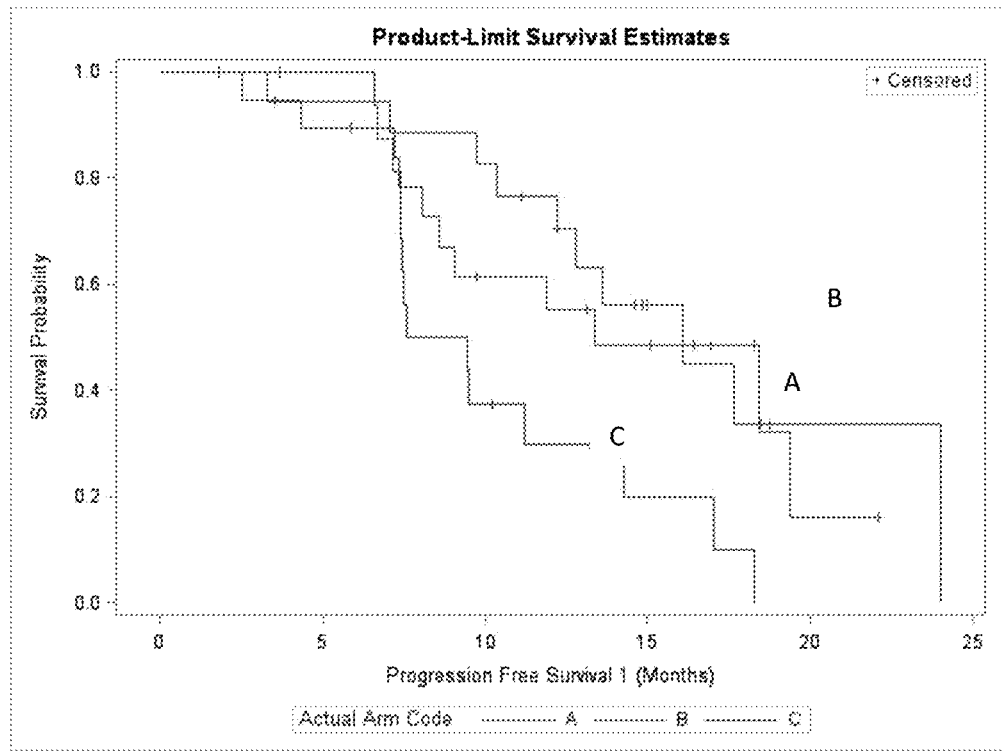
FIG. 2 illustrates Kaplan Meier graphs comparing treatment of RAS wild-type patients.
Figure 2:
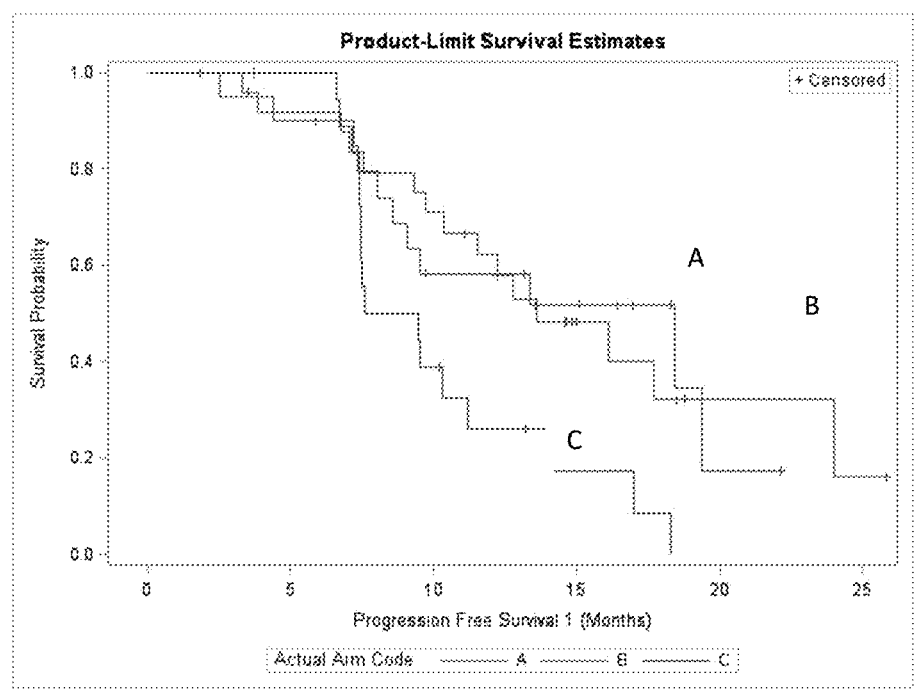
Figure 3:
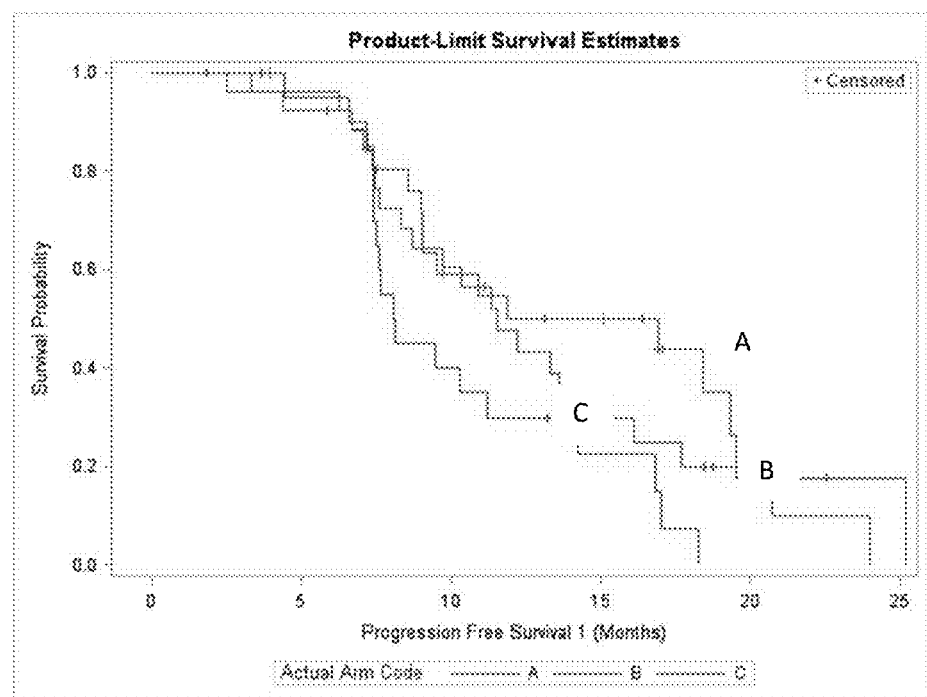
FIG. 3 illustrates Kaplan Meier graphs comparing treatment of TP53 mutant patients.
Figure 3:
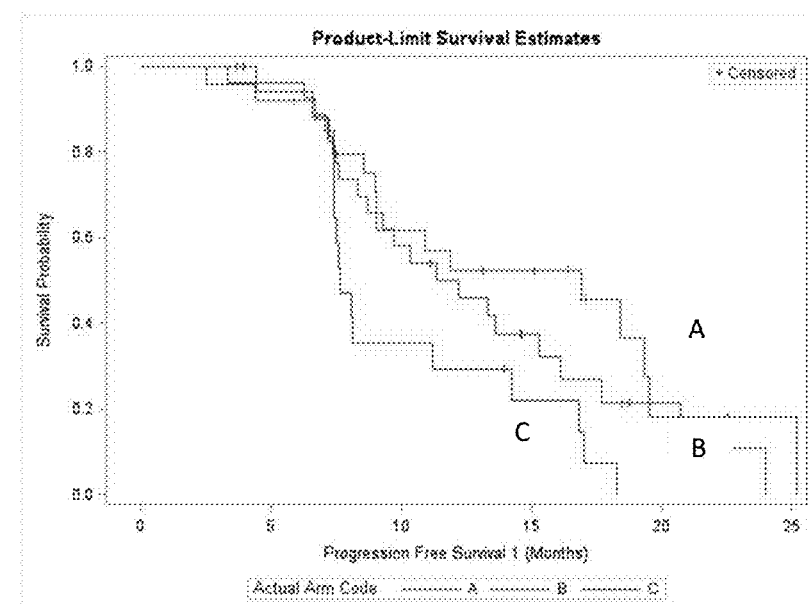
Figure 4:
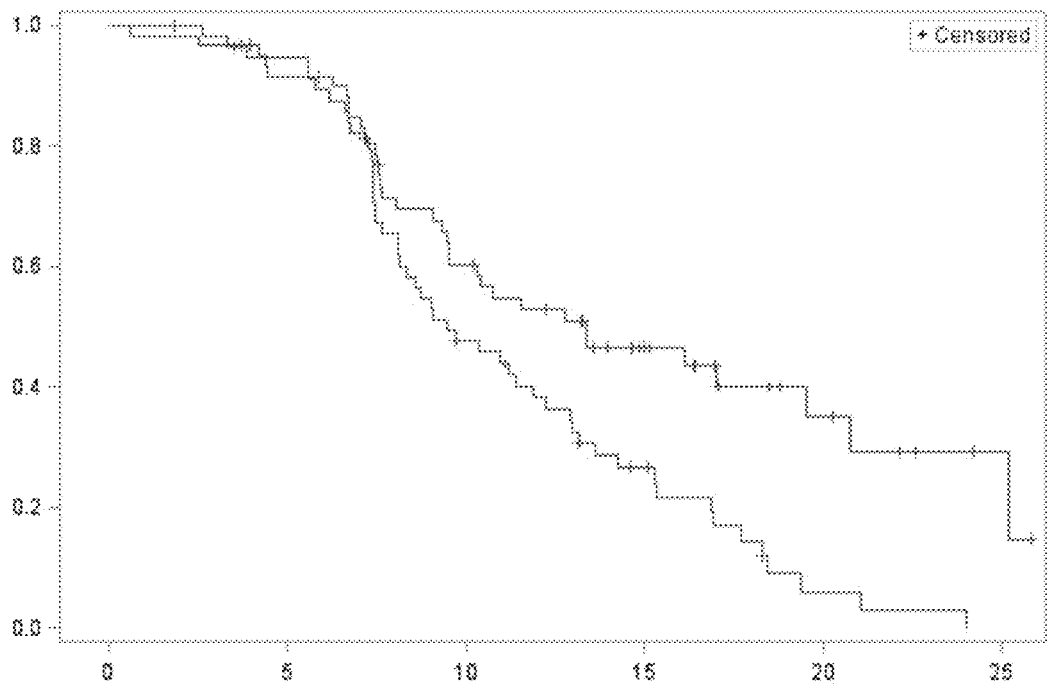
FIG. 4 illustrates Kaplan Meier graphs comparing treatment outcomes of patients with different mutation burdens (mutant allele frequencies, AF).
Figure 4:
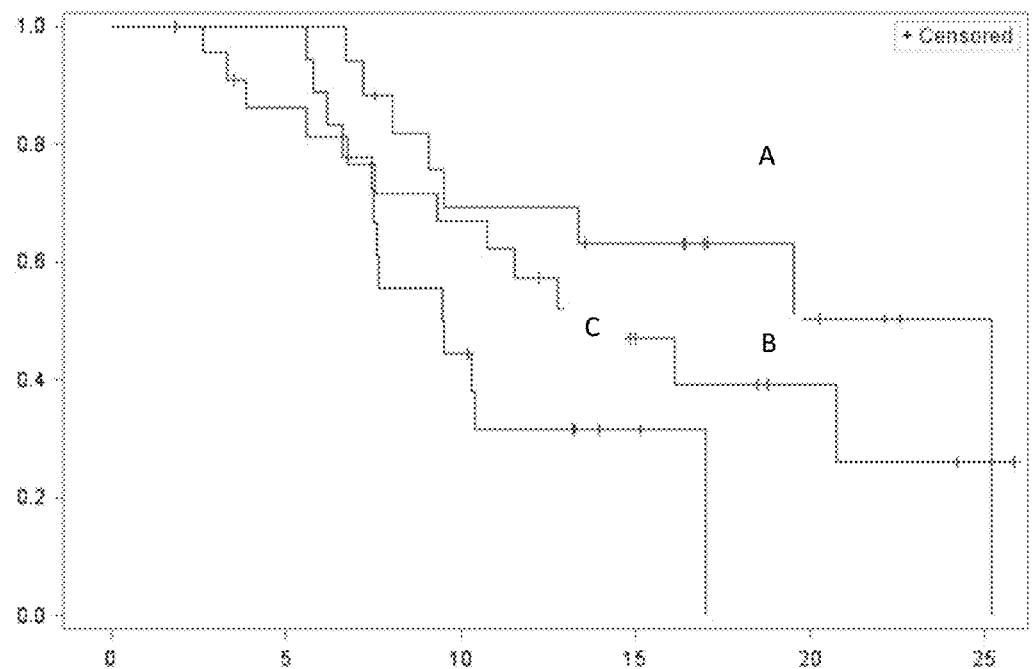

The inventors have devised a method of using RAS mutation status to prescribe a treatment regimen. Surprisingly, the inventors have found that RAS wild-type patients and KRAS wild-type patients (as determined by applying the mutation test of the invention to pre-induction plasma samples) showed significantly longer progression-free survival (PFS) in both cFOLFOXIRI-BEV (A) and sFOLFOXIRI-BEV (B) arms versus FOLFOX-BEV (C) (FIG. 2). In FIGS. 2, 3 and 4, as in Table 2, treatment A is concurrent treatment with FOLFOXIRI-bevacizumab (cFOLFOXIRI-BEV), treatment B is sequential treatment with FOLFOXIRI-bevacizumab (sFOLFOXIRI-BEV) and treatment C is treatment with FOLFOX-bevacizumab (FOLFOXI-BEV). The inventors also saw this result using genotyping of tissue samples. This was not seen in RAS or KRAS mutant patients. In some embodiments, the invention comprises testing a patient's sample for mutations in the RAS gene (KRAS and NRAS) or KRAS gene prior to commencement of chemotherapy. In some embodiments, the pre-treatment sample is a tumor tissue sample. In other embodiments the sample is blood sample. In some embodiments, the treatment selected from consecutive and sequential FOLFOXIRI-bevacizumab. In some embodiments, the invention is a method of treating a patient with metastatic CRC comprising testing a patient's sample for mutations in the RAS gene (KRAS and NRAS) or KRAS gene and if no mutations are found, administering therapy selected from consecutive and sequential FOLFOXIRI-bevacizumab.

Further, the inventors have devised a method of using BRAF mutation status to prescribe a treatment regimen. The inventors found that BRAF wild-type patients (as determined by applying the mutation test of the invention to pre-induction plasma samples) showed significantly longer progression-free survival (PFS) in both cFOLFOXIRI-BEV (A) and sFOLFOXIRI-BEV (B) arms versus FOLFOX-BEV (C). The inventors also saw this result using genotyping of tissue samples. This was not seen in BRAF mutant patients. In some embodiments, the invention comprises testing a patient's sample for mutations in the BRAF gene prior to commencement of chemotherapy. In some embodiments, the pre-treatment sample is a tumor tissue sample. In other embodiments the sample is blood sample. In some embodiments, the treatment selected from consecutive and sequential FOLFOXIRI-bevacizumab. In some embodiments, the invention is a method of treating a patient with metastatic CRC comprising testing a patient's sample for mutations in the BRAF gene and if no mutations are found, administering therapy selected from consecutive and sequential FOLFOXIRI-bevacizumab.

Further, the inventors have devised a method of using PIK3CA mutation status to prescribe a treatment regimen. The inventors found that PIK3CA wild-type patients (as determined by applying the mutation test of the invention to pre-induction plasma samples) showed significantly longer progression-free survival (PFS) in both cFOLFOXIRI-BEV (A) and sFOLFOXIRI-BEV (B) arms versus FOLFOX-BEV (C). The inventors also saw this result using genotyping of tissue samples. This was not seen in PIK3CA mutant patients. In some embodiments, the invention comprises testing a patient's sample for mutations in the PIK3CA gene prior to commencement of chemotherapy. In some embodiments, the pre-treatment sample is a tumor tissue sample. In other embodiments the sample is blood sample. In some embodiments, the treatment selected from consecutive and sequential FOLFOXIRI-bevacizumab. In some embodiments, the invention is a method of treating a patient with metastatic CRC comprising testing a patient's sample for mutations in the PIK3CA gene and if no mutations are found, administering therapy selected from consecutive and sequential FOLFOXIRI-bevacizumab.

Yet further, the inventors have devised a method of using TP53 mutation status to prescribe a treatment regimen. The inventors have found that TP53 WT showed no significant treatment differences while TP53 MUT showed longer PFS for cFOLFOXIRI-BEV versus FOLFOX-BEV (FIG. 3). In some embodiments, the invention comprises testing a patient's sample for mutations in the TP53 gene prior to commencement of chemotherapy. In some embodiments, the pre-treatment sample is a tumor tissue sample. In other embodiments the sample is blood sample. In some embodiments, the treatment selected from consecutive and sequential FOLFOXIRI-bevacizumab. In some embodiments, the invention is a method of treating a patient with metastatic CRC comprising testing a patient's sample for mutations in the TP53 gene and if mutations are found, administering therapy selected from consecutive and sequential FOLFOXIRI-bevacizumab.

The findings described above and illustrated in Table 2 underscore the unpredictability of the mutations in oncogenes and antioncogenes. While the wild-type status of the RAS, BRAF and PIK3CA oncogenes has a positive effect on response, the wild-type status of the TP53 antioncogene has no positive effect. At the same time, the mutant status of the RAS, BRAF and PIK3CA oncogenes has no positive effect on response to therapy, while mutant status of the TP53 antioncogene has a positive effect on response to therapy. Further underscoring unpredictability, the mutation status is more relevant to some types of therapy than others, e.g., FOLFOXIRI-bevacizumab but not FOLFOX-bevacizumab.

The inventors have further devised a method of using mutant allele frequency (mAF) to prescribe a treatment regimen. As shown in Table 3 and FIG. 4, the inventors have discovered that patients with a pre-induction mAF below the median had longer PFS compared to patients with mAF above the median (13.4 vs 9.5 mo, HR 0.49, p=0.002). A similar trend was seen for overall survival (OS). Within the below median mAF group, longer PFS was observed in patients treated with cFOLFOXIRI-BEV versus FOLFOX-BEV (25.2 vs 9.5 mo, HR 0.34, p=0.020). In contrast, no differences in PFS were observed in the treatment arms in the above median mAF group. Patients with a post-induction mAF below the median had longer PFS compared to patients with mAF above the median (15.3 vs 8.1 mo, HR 0.51, p=0.0064). In some embodiments, the invention comprises testing a patient's sample to determine mutant allele frequencies (mAF) in cancer associated genes prior to commencement of chemotherapy. In some embodiments, the cancer associated genes are those listed in Table 1. In some embodiments, the pre-treatment sample is a tumor tissue sample. In other embodiments the sample is blood sample. In some embodiments, the treatment selected from consecutive and sequential FOLFOXIRI-bevacizumab. In some embodiments, the invention is a method of treating a patient with metastatic CRC comprising testing the patient's sample for testing the patient's sample to determine mutant allele frequencies (mAF) in cancer associated genes and if the frequencies are below the median observed in mCRC patients, administering therapy selected from consecutive and sequential FOLFOXIRI-bevacizumab.

In some embodiments, the invention further includes a step of improving the biomarker panel based on the results obtained from the clinical samples. In some embodiments, the invention includes the steps of analyzing the correlation between the presence of a biomarker in the cell-free DNA and response to therapy. The biomarkers showing a predictive correlation are to be included in the panel predicting response to particular therapy. The biomarkers not showing a statistically significant predictive correlation are to be excluded from the panel predicting response to the therapy.

The invention includes a step of identifying the patient as likely or not likely to respond to a therapy regimen. The identification is based on whether the mutations in the biomarkers of the panel were found during the sequencing step. In some embodiments, several mutations, e.g., mutations in 1, 2, 3, 4 or more biomarkers are found while no mutations in other biomarkers are found.

In some embodiments, the method includes an analysis algorithm for scoring the mutations identified during the sequencing step. The algorithm may contain steps of mutation detection, mutation frequency scoring, error correction (including deduplication, using barcodes to eliminate errors) and final determination whether the sample is mutation-positive. In some embodiments, the sample is scored as mutation-positive for a particular biomarker from the panel when the frequency of a mutated allele (variant allele frequency, VAF) exceeds a certain threshold. In some embodiments, the threshold is 5% but other thresholds may be used based on the condition of the sample. For example, a tumor sample with low tumor content may have a lower threshold (e.g., <5% of mutant allele frequency, VAF) for the sample to be scored as mutation-positive. In some embodiments, the algorithm also accounts for the germ-line variations in the biomarkers. For example, a biomarker known to have high level of variation in the germline (>1% ExAC, FIG. 1) may not be scored as mutant.

This invention advances the field of mCRC treatment management of patients by identifying gene mutations or mutation allele fractions as a method to predict progression free survival in response to a therapy regimen. The method is applicable to metastatic CRC patients and, since these chemotherapeutic agents are also used in stage II/III patients, the method may be applicable to these stages as well.

EXAMPLES

Example 1

Using Cell Free Tumor DNA in Metastatic Colorectal Cancer (mCRC) Patients to Predict Efficacy of Therapies In this example, the next-generation sequencing based AVENIO® ctDNA Expanded Kit (Roche Sequencing Solutions, Pleasanton, Calif.) was used to identify somatic mutations and mutation burden in 77 cancer-related genes by next-generation sequencing (NGS) in both pre- and post-induction plasma samples (n=118 for both groups) from STEAM. STEAM (NCT01765582) evaluated the efficacy and safety of concurrent (c) and sequential (s) FOLFOXIRI-bevacizumab (BEV) versus FOLFOX-BEV for first-line treatment of mCRC. Matched baseline tissue and pre-induction plasma showed a concordance rate of 83% across all genes and 91.5%-100% for known mCRC related biomarkers. Four mutation classes including single-nucleotide variants (SNVs), indels, copy number amplifications (CNAs) and fusions were identified. SNVs and indels were called in tissue and plasma at allele frequencies of 5% and 0.25% respectively.

Overall, patients with a pre-induction mutant allele frequency (mAF) below the median had longer PFS compared to patients with mAF above the median (13.4 vs 9.5 mo, HR 0.49, p=0.002). A similar trend was seen for overall survival (OS). Within the below median mAF group, longer PFS was observed in patients treated with cFOLFOXIRI-BEV versus FOLFOX-BEV (25.2 vs 9.5 mo, HR 0.34, p=0.020). In contrast, no differences in PFS were observed in the treatment arms in the above median mAF group. Patients with a post-induction mAF below the median had longer PFS compared to patients with mAF above the median (15.3 vs 8.1 mo, HR 0.51, p=0.0064).

We claim:

1. A method for identifying a colorectal cancer patient in stage II, III, or IV as likely to positively respond to a chemotherapy regimen with increased progression-free survival (PFS), wherein the method comprises the steps of:
   (a) obtaining a cell-free blood sample obtained from the patient;
   (b) sequencing nucleic acid from the cell-free blood sample, to detect the presence of one or more mutations in at least a portion of each of APC, BRCA1, BRCA2, EGFR, ERBB2, ALK, BRAF, DPYD, AR, CCND1, CCND2, CCND3, CD274, KRAS, MET, TP53, KIT, NRAS, PDGFRA, RET, ROS1, MSH2, MSH6, NF2, PDCD1LG2, PMS2, ABL1, AKT1, AKT2, ARAF, CDK6, CSF1R, CTNNB1, DDR2, EZH2, FGFR1, FGFR2, CDK4, CDKN2A, FGFR3, FLT1, FLT3, FLT4, GATA3, GNA11, GNAQ, GNAS, IDH1, IDH2, JAK2, ESR1, FBXW7, JAK3, KDR, MAP2K1, MAP2K2, MTOR, NFE2L2, NTRK1, PDGFRB, PIK3CA, PIK3R1, PTCH1, KEAP1, MLH1, RAF1, RNF43, TERT promoter, TSC1, TSC2, PTEN, RB1, SMAD4, SMO, STK11, VHL, and UGT1A1, wherein a frequency of the one or more mutations being below a median documented for colorectal cancer patients at the same stage indicates the patient as likely to positively respond to the chemotherapy regimen if the frequency of mutant alleles is below a median documented for colorectal cancer patients at the same stage, and wherein a frequency of the one or more mutations being above a median documented for colorectal cancer patients at the same stage indicates the patient is not likely to positively respond to the chemotherapy regimen; and
   (c) administering the chemotherapy regimen if the patient is identified as likely to positively respond to the chemotherapy regimen, and
   wherein the chemotherapy regimen comprises a treatment with FOLFOXIRI-bevacizumab or a treatment with FOLFOX-bevacizumab.

2. The method of claim 1, wherein the treatment with FOLFOXIRI-bevacizumab is selected from concurrent and sequential.

3. A method of treatment of a colorectal cancer patient in stage II, III, or IV, wherein the method comprises the steps of:
   (a) providing a cell-free blood sample obtained from the patient;
   (b) sequencing at least a portion of each of APC, BRCA1, BRCA2, EGFR, ERBB2, ALK, BRAF, DPYD, AR, CCND1, CCND2, CCND3, CD274, KRAS, MET, TP53, KIT, NRAS, PDGFRA, RET, ROS1, MSH2, MSH6, NF2, PDCD1LG2, PMS2, ABL1, AKT1, AKT2, ARAF, CDK6, CSF1R, CTNNB1, DDR2, EZH2, FGFR1, FGFR2, CDK4, CDKN2A, FGFR3, FLT1, FLT3, FLT4, GATA3, GNA11, GNAQ, GNAS, IDH1, IDH2, JAK2, ESR1, FBXW7, JAK3, KDR, MAP2K1, MAP2K2, MTOR, NFE2L2, NTRK1, PDGFRB, PIK3CA, PIK3R1, PTCH1, KEAP1, MLH1, RAF1, RNF43, TERT promoter, TSC1, TSC2, PTEN, RB1, SMAD4, SMO, STK11, VHL, and UGT1A1;
   (c) measuring the frequency of mutant alleles; and
   (d)(i) identifying the patient as likely to positively respond to a chemotherapy regimen if the frequency of mutant alleles is below a median documented for colorectal cancer patients at the same stage; or
   (d)(ii) identifying the patient as not likely to positively respond to the chemotherapy regimen if the frequency of mutant alleles is above a median documented for colorectal cancer patients at the same stage; and
   (e) administering the chemotherapy regimen to the patient identified as likely to positively respond to the chemotherapy regimen, and
   wherein the chemotherapy regimen comprises a treatment with FOLFOXIRI-bevacizumab or a treatment with FOLFOX-bevacizumab.

4. The method of claim 3, wherein the chemotherapy regimen comprises concurrent FOLFOXIRI-bevacizumab or sequential FOLFOXIRI-bevacizumab.

* * * * *